United States Patent
Doi (10) Patent No.: US 10,617,856 B2
(45) Date of Patent: Apr. 14, 2020

(54) BALLOON CATHETER

(71) Applicant: TERUMO KABUSHIKI KAISHA, Shibuya-ku, Tokyo (JP)

(72) Inventor: Yuta Doi, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 262 days.

(21) Appl. No.: 15/653,078

(22) Filed: Jul. 18, 2017

(65) Prior Publication Data

US 2017/0312487 A1     Nov. 2, 2017

Related U.S. Application Data

(63) Continuation of application No. PCT/JP2015/084749, filed on Dec. 11, 2015.

(30) Foreign Application Priority Data

Jan. 26, 2015  (JP) .................................. 2015-012236

(51) Int. Cl.
  *A61M 29/02*    (2006.01)
  *A61M 25/10*    (2013.01)
  *A61M 39/06*    (2006.01)

(52) U.S. Cl.
  CPC ........ *A61M 29/02* (2013.01); *A61M 25/1006* (2013.01); *A61M 39/06* (2013.01);
  (Continued)

(58) Field of Classification Search
  CPC .. A61M 29/02; A61M 39/06; A61M 25/1006; A61M 25/10184;
  (Continued)

(56) References Cited

U.S. PATENT DOCUMENTS

| 4,941,877 A |   | 7/1990 | Montano, Jr. |
| 5,087,246 A | * | 2/1992 | Smith ............... A61M 25/1038 604/103 |

(Continued)

FOREIGN PATENT DOCUMENTS

| JP | 5-269207 A | 10/1993 |
| JP | 2002-336359 A | 11/2002 |

OTHER PUBLICATIONS

International Search Report (PCT/ISA/210) dated Mar. 8, 2016, by the Japanese Patent Office as the International Searching Authority for International Application No. PCT/JP2015/084749.

(Continued)

*Primary Examiner* — Julian W Woo (74) *Attorney, Agent, or Firm* — Buchanan Ingersoll & Rooney PC (57) ABSTRACT

A balloon catheter including an elongated catheter main body portion and a balloon provided on the distal portion of the catheter main body portion. The balloon is inflatable to expand radially outward into an inflated state and deflatable to contract radially inward into a deflated state. The catheter main body portion includes a hollow outer tube and a hollow inner tube disposed within the outer tube. The balloon includes a contact portion that contacts the outer surface of the inner tube and a vane portion protruding from the contact portion radially outward when the balloon is in the deflated state. The contact portion of the balloon includes a connecting portion that connects the balloon to the catheter main body portion.

17 Claims, 8 Drawing Sheets

(52) U.S. Cl.
CPC ............... *A61M 25/10184* (2013.11); *A61M 2025/1004* (2013.01); *A61M 2025/1084* (2013.01); *A61M 2205/0216* (2013.01)

(58) Field of Classification Search
CPC .. A61M 2025/1084; A61M 2025/1004; A61M 2205/0216
See application file for complete search history.

(56) References Cited

U.S. PATENT DOCUMENTS

| | | | | |
|---|---|---|---|---|
| 5,147,302 | A * | 9/1992 | Euteneuer | A61M 25/1038 604/103 |
| 5,226,887 | A | 7/1993 | Farr et al. | |
| 5,383,856 | A * | 1/1995 | Bersin | A61M 25/1002 604/101.01 |
| 5,792,172 | A * | 8/1998 | Fischell | A61F 2/958 606/194 |
| 5,840,064 | A * | 11/1998 | Liprie | A61N 5/1002 604/103.07 |
| 6,425,882 | B1 | 7/2002 | Vigil | |
| 6,544,224 | B1 * | 4/2003 | Steese-Bradley | A61M 25/1002 604/103.06 |
| 7,744,620 | B2 * | 6/2010 | Pedersen | A61B 17/22 606/194 |
| 7,857,786 | B2 * | 12/2010 | Burton | A61M 25/10 604/103.14 |
| 7,887,557 | B2 | 2/2011 | Kelley et al. | |
| 9,895,517 | B2 * | 2/2018 | Tilson | A61M 25/10185 |

OTHER PUBLICATIONS

Written Opinion (PCT/ISA/237) dated Mar. 8, 2016, by the Japanese Patent Office as the International Searching Authority for International Application No. PCT/JP2015/084749.

* cited by examiner

FIG. 16

BALLOON CATHETER

CROSS-REFERENCES TO RELATED APPLICATIONS

This application is a continuation of International Application No. PCT/JP2015/084749 filed on Dec. 11, 2015, and claims priority to Japanese Patent Application No. 2015-012236 filed on Jan. 26, 2015, the entire content of both of which is incorporated herein by reference.

TECHNICAL FIELD

The present invention generally relates to a balloon catheter including a balloon on a distal end portion of the balloon catheter.

BACKGROUND DISCUSSION

A balloon catheter is widely used to ameliorate lesion areas (stenotic lesions) generated in a body lumen of a living body. The balloon catheter typically includes an elongated catheter main body portion and a balloon provided on a distal side of the catheter main body portion. The balloon can be inflated in a radial direction (i.e., is inflatable to expand radially outward). The balloon catheter is configured such that the deflated balloon is advanced to a location of interest in a body via a narrow body lumen and then the balloon of the balloon catheter is inflated, whereby a lesion area in the living body can be widened.

The catheter main body portion includes a hollow outer tube and a hollow inner tube. The inner tube is disposed within a hollow interior of the outer tube. A distal-side end portion of the outer tube is fixed to a proximal side of the balloon and the hollow interior of the outer tube forms an inflation lumen that communicates with the interior of the balloon. The balloon can be inflated by infusing an inflation fluid into the balloon via the inflation lumen at the time of treatment (i.e., when the balloon is positioned at the lesion area). A distal-side end portion of the inner tube is fixed to a distal side of the balloon, and a hollow interior of the inner tube forms a guide wire lumen into which a guide wire can be inserted.

The treatment by the balloon catheter is conducted in the following manner. First, the guide wire is inserted into a body lumen of a living body to pass through a lesion area. The balloon catheter is then inserted into the body lumen along the guide wire (i.e., the balloon catheter is moved into the living body along the guide wire) to deliver the balloon to the lesion area. The balloon is inflated at the lesion area, thereby proceeding with the treatment (e.g., widening the stenosis region of the body lumen). Subsequently, the balloon is deflated (subjected to deflation) and the balloon catheter is removed from within the body.

A manipulation (i.e., operations) of inflating and then deflating the balloon and inflating the balloon again at the same location, or a manipulation (i.e., operations) of inflating the balloon in one lesion area, then deflating the balloon, moving the balloon to another lesion area, and inflating the balloon again is often performed depending on a state of the lesion area or the number of lesion areas.

As described above, balloon catheter operations include inserting the balloon catheter into a narrow body lumen, moving the balloon catheter, and withdrawing the balloon catheter from the living body. Therefore, a balloon catheter needs to exhibit an excellent passing performance for moving within the body lumen (i.e., movability or maneuverability within the body lumen). Since an outer diameter of the balloon of the balloon catheter is relatively large, the balloon must be deflated (i.e., in a tight state against the catheter main body portion) as much as possible. The balloon is thus collapsed during deflation into a shape with a contact portion in contact with the inner tube and a plurality of vane portions protruding from the contact portion in a radial direction.

When the balloon is inflated and then deflated, the balloon returns to this original shape with the contact portion and the vane portions. When the inflation and the deflation operations are repeated, however, the balloon in the deflated state often loses the shape (i.e., the shape with the contact portion and the vane portions). For example, the original shape of the balloon in the deflated state may be one that has three vane portions that are each disposed at an angle of 120 degrees in a circumferential direction (i.e., the three vane portions are evenly spaced apart in the circumferential direction). Contact portions are provided between the vane portions. When a balloon of this configuration is repeatedly inflated and deflated a plurality of times, the contact portions do not completely return to original shapes and the adjacent vane portions may become connected together, so that the shape of the balloon often changes over time to a shape with two vane portions. Decreasing the number of vane portions causes the protrusion length of one vane portion to increase. Moreover, the shapes of the vane portions become uneven because of the difference of the number of vane portions from the original number. As a result, an outer diameter of the balloon of the balloon catheter increases, resulting in the degradation of the passing performance (i.e., maneuverability) of the balloon catheter.

As outlined by the above discussion, a balloon catheter is required to exhibit excellent re-wrappability to help ensure that the balloon returns to the original shape when being deflated after inflation. Japanese Patent Application Publication No. 2002-336359 discloses an example of a technique for attaching a metallic external member including a band and fingers to a balloon from outside and disposing the fingers at positions of contact portions. The fingers can compress the contact portions to return the contact portions to the original positions when the balloon is deflated.

SUMMARY

When the external member is attached to the balloon from the outside as described in Japanese Patent Application Publication No. 2002-336359, however, the outer diameter of the balloon increases by as much as the magnitude of the external member. This increase in outer diameter of the balloon results in the degradation of the passing performance of the balloon catheter. Furthermore, flexural rigidity is quite high since the external member is made of metal. The flexibility of the balloon is thus hampered and the fingers can cause the balloon to burst. Moreover, the external member can fall off the balloon when the external member is provided on the balloon from outside.

The balloon catheter disclosed in this application is capable of improving re-wrappability of a balloon without the need to attach an external member to the balloon from outside.

A balloon catheter includes an elongated catheter main body portion extending in an axial direction. The catheter main body portion possesses a distal portion and a proximal portion proximal to the distal portion in the axial direction. The balloon catheter includes a balloon provided on the distal portion of the catheter main body portion. The balloon is inflatable to expand radially outward into an inflated state and deflatable to contract radially inward into a deflated state. The catheter main body portion includes a hollow outer tube and a hollow inner tube disposed within the outer tube. The outer and inner tubes extend in the axial direction. The outer and inner tubes each possess an inner surface and an outer surface. The balloon includes a contact portion that contacts the outer surface of the inner tube and a vane portion protruding from the contact portion radially outward when the balloon is in the deflated state. The contact portion of the balloon includes a connecting portion that connects the balloon to the catheter main body portion.

The contact portion of the balloon catheter described above is always connected to the inner tube by the connecting portion even when the balloon is repeatedly inflated and deflated a plurality of times. This balloon catheter configuration helps ensure that the balloon returns to its original shape when the balloon is deflated. That is, it is possible to improve the re-wrappability of the balloon without the need to attach the external member to the balloon from outside.

The proximal side of the balloon is fixed to the outer tube, a distal side of the balloon is fixed to the inner tube, and the connecting portion may be formed by being fixedly bonded to a peripheral surface of either the outer tube or the inner tube. This configuration may allow the connecting portion to be formed only by fixedly bonding the balloon to the peripheral surface of either the outer tube or the inner tube. It is thus possible to facilitate manufacturing.

The balloon of the balloon catheter may include a large-diameter portion having a diameter larger from the proximal side toward the distal side, an equal-diameter portion continuous with the large-diameter portion and having a generally equal diameter along an axial direction, and a decreased-diameter portion continuous with the equal-diameter portion and having a diameter smaller from the proximal side to the distal side. The connecting portion may not be present in the equal-diameter portion, so that it is possible to avoid an influence as much as possible of the connecting portion on the shape of the equal-diameter portion that is an effective portion during treatment.

The connecting portion may be formed by linearly and fixedly bonding the balloon to the inner tube from a fixedly bonded portion where the balloon is fixed to either the outer tube or the inner tube to a central side of the balloon. Forming the connection portion in this manner may increase the connection strength for connecting the balloon to the inner tube by the connecting portion and help prevent separation (rupture) of the connecting portion when the balloon is inflated.

The connecting portion can be formed by fixedly bonding the balloon to the inner tube in a dot manner from a fixedly bonded portion where the balloon is fixed to either the outer tube or the inner tube to a central side of the balloon. The fixedly bonded area can be made small by this manner of bonding, and it is, therefore, possible to facilitate manufacturing.

An end portion of the connecting portion, which is closer to the central side of the balloon, may be formed into a smooth curved shape. The connecting portion may thus avoid stress concentration on the central-side end portion of the connecting portion, and help to prevent separation (rupture) of the connecting portion when the balloon is inflated.

The proximal side of the balloon is fixed to the outer tube, a distal side of the balloon is fixed to the inner tube, and the connecting portion may be formed from an elastic material suspended between the balloon and either the outer tube or the inner tube. The connecting portion can thus be provided in a broad range of the balloon including the equal-diameter portion by appropriately setting elasticity of the connecting portion. Furthermore, it is possible to avoid an influence of the connecting portion on the shape of the equal-diameter portion that is an effective portion during treatment as much as possible.

The inner tube of the balloon catheter may include an outer peripheral member in at least a part of an outer periphery within the balloon and the connecting portion can connect the balloon to the outer peripheral member. The outer peripheral member is not constrained to a peripheral surface of the inner tube in a range in which at least the connecting portion is connected to the outer peripheral member in the axial direction, so that it is possible to help prevent the inner tube from being pulled outward by the connecting portion when the balloon is inflated. It is thus possible to help prevent degradation of a slidability of the guide wire due to the expansion of the inner tube.

The inner tube of the balloon catheter may include a reinforcement portion having an increased strength in a range connected by at least the connecting portion in the axial direction so that it is possible to help prevent degradation of the slidability of the guide wire due to a reduction of strength of a pulled portion of the inner tube even if the inner tube is pulled outward by the connecting portion when the balloon is inflated.

In another aspect, a balloon catheter includes an elongated catheter main body portion extending in an axial direction from a proximal end to a distal end. The catheter main body portion includes a cylindrical outer tube and a cylindrical inner tube within the outer tube. The outer tube possesses a distal end and the inner tube extends in the axial direction distally beyond the distal end of the outer tube. The inner and outer tubes each possess an inner surface and an outer surface. A balloon is connected to the inner tube and to the outer tube of the catheter main body portion. The balloon is inflatable to expand radially outward into an inflated state and deflatable to contract radially inward into a deflated state. A plurality of connecting portions fixedly bond the inner surface of the balloon to the outer surface of at least one of the inner tube and the outer tube. The connecting portions are spaced apart from one another in the circumferential direction. The balloon includes a plurality of vane portions. Each of the vane portions are adjacent to the connecting portions so that the vane portions and the connecting portions alternate in the circumferential direction. The vane portions protrude radially outward beyond the balloon at the connecting portions when the balloon is in the deflated state. The vane portions of the balloon inflating and extending radially outwardly when the balloon is in the inflated state. The connecting portions preventing the balloon from expanding radially outward at the connecting portions during inflation.

This disclosure also relates to a method of treating a lesion area in a living body using a balloon catheter. The method includes moving the balloon catheter within the living body to the lesion area, the balloon catheter comprising an elongated main body extending in an axial direction and a balloon fixed to the elongated main body, the balloon possessing an outer diameter and a circumferential direction, the balloon being inflatable to expand radially outward into an inflated state and deflatable to contract radially inward into a deflated state, the balloon being in the deflated state during the moving of the balloon catheter within the living body to the lesion area. The method further includes positioning the balloon of the balloon catheter in the lesion area, the outer diameter of the balloon being smaller than an inner diameter of the lesion area, and inflating the balloon of the balloon catheter while the balloon catheter is positioned at the lesion area so that the balloon expands radially outward into contact with the lesion area to widen the lesion area of the living body. Circumferentially spaced apart vane portions of the balloon expand radially outwardly when the balloon is inflated while circumferentially spaced apart non-inflation portions of the balloon do not expand radially outwardly. The vane portions and the non-inflation portions axially overlap one another. The balloon includes vane portions that extend radially outward from the elongated main body and connected portions between the vane portions in the circumferential direction. The method includes deflating the balloon to contract the balloon radially inwardly into the deflated state and removing the balloon catheter from the lesion area of the living body

DETAILED DESCRIPTION

Set forth below with reference to the accompanying drawings is a detailed description of embodiments of a balloon catheter representing examples of the inventive balloon catheter disclosed here It is noted that a scale ratio of the drawings is exaggerated for the convenience of description and often differs from an actual scale ratio. In the present description, a side of a balloon catheter 10 inserted into a body lumen will be referred to as "distal end" or "distal side" while a handling hand side thereof will be referred to as "proximal end" or "proximal side".

Figure 1:
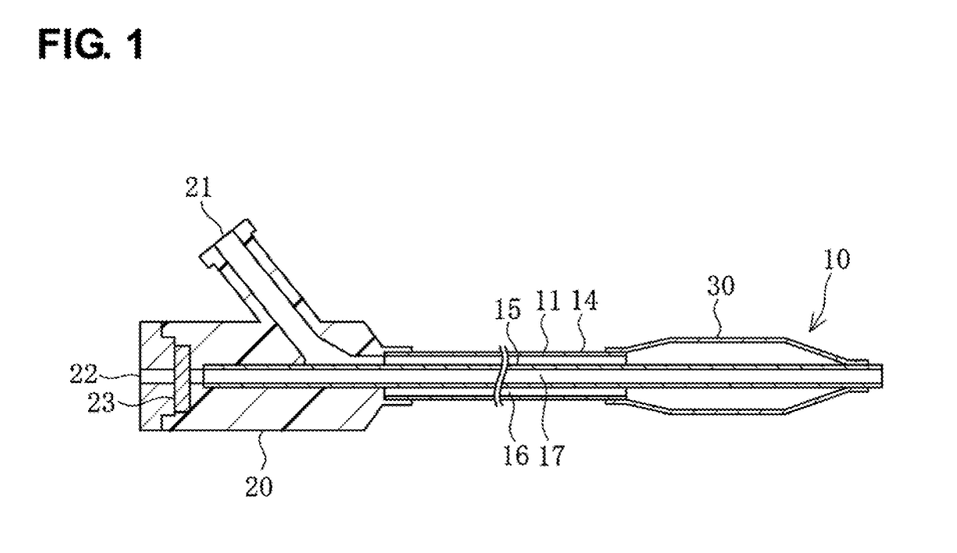
FIG. 1 is a cross-sectional view illustrating an overall structure of a balloon catheter.

First, a configuration of the balloon catheter 10 is described. As shown in FIG. 1, the balloon catheter 10 includes an elongated and hollow catheter main body portion 11, a balloon 30 provided on a distal end portion of the catheter main body portion 11, and a hub 20 fixedly bonded to a proximal end of the catheter main body portion 11.

The catheter main body portion 11 includes an outer tube 14 that is a hollow tube-shaped body (i.e., cylindrical) and an inner tube 15 that is disposed within the outer tube 14. An inflation lumen 16 is formed between the outer tube 14 and the inner tube 15. The inflation lumen 16 is configured to receive/circulate an inflation fluid for inflating the balloon 30. A guide wire lumen 17 into which a guide wire (not shown) is inserted is formed inside the inner tube 15.

The outer tube 14 and the inner tube 15 are preferably each formed from a material exhibiting a certain degree of flexibility (i.e., a relatively flexible material). Examples of such a material to be used include polyolefin such as polyethylene, polypropylene, polybutene, ethylene-polypropylene copolymer, ethylene-vinyl acetate copolymer, ionomer, and mixtures of two or more types of the above polymers, fluorocarbon resin such as soft polyvinyl chloride resin, polyamide, polyamide elastomer, polyester, polyester elastomer, polyurethane, and polytetrafluoroethylene, silicone rubber, and latex.

The balloon 30 is formed from a material exhibiting flexibility (i.e., a relatively flexible or elastic material) similarly to the outer tube 14 and the inner tube 15. A highly flexible material is preferably selected as the material of the balloon 30 based on the intended operation of the balloon 30. FIG. 1 shows the balloon 30 in a deflated state. In general, the cross-sectional views taken along an axial direction in the various drawings of this application typically illustrate the balloon 30 in the deflated state or the inflated state.

A distal side of the balloon 30 is fixedly bonded to the inner tube 15, a proximal side of the balloon 30 is fixedly bonded to the outer tube 14, and an interior of the balloon 30 is in communication with the inflation lumen 16. It is thereby possible to inflate the balloon 30 by infusing the inflation fluid into the balloon 30 via the inflation lumen 16. The inflation fluid may be either a gas or a liquid. For example, a gas such as helium gas, CO2 gas, or O2 gas, or a liquid such as a physiological salt solution or a contrast agent can be used as the inflation fluid.

The hub 20 includes a first opening portion 21 that functions as a port which communicates with the inflation lumen 16 formed between the outer tube 14 and the inner tube 15. Inflation fluid flows into or out of the first opening portion and the inflation lumen 16. The hub 20 includes a second opening portion 22 that communicates with the guide wire lumen 17. A hemostasis valve 23 is provided in the second opening portion 22. The hemostasis valve 23 inhibits the outflow of blood while the guide wire 1 is allowed to be freely inserted into the hemostasis valve 23.

Figure 2:
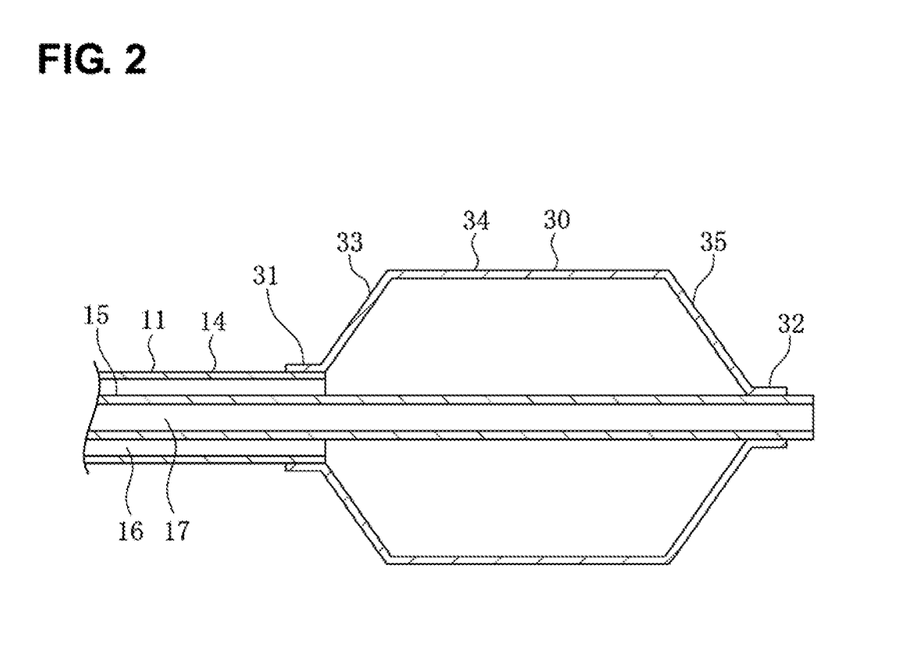
FIG. 2 is an enlarged cross-sectional view of the vicinity of an inflated balloon.

A structure of the balloon 30 is described in detail next. As shown in FIG. 2, a proximal-side end portion of the balloon 30 is a proximal-side fixedly bonded portion 31 fusion bonded to a peripheral surface of the outer tube 14. In other words, the inner surface of the proximal end of the balloon 30 is bonded directly to the outer surface of the outer tube 14 as shown in FIG. 2. The balloon 30 includes a large-diameter portion 33 having an outer diameter that is larger from the proximal-side fixedly bonded portion 31 toward the distal side (i.e., the outer diameter of the large-diameter portion 33 gradually increases from the proximal end to the distal end of the large-diameter portion 33), an equal-diameter portion 34 continuous with the large-diameter portion 33 and having a generally equal outer diameter along the axial direction of the catheter main body portion 11, and a decreased-diameter portion 35 continuous with the equal-diameter portion 34 and having an outer diameter smaller toward the distal side (i.e., the outer diameter gradually decreases from the proximal end at the equal-diameter portion 34 to the distal end of the decreased-diameter portion 35). The distal-side end portion of the balloon 30 is a distal-side fixedly bonded portion 32 fusion bonded to a peripheral surface of the inner tube 15. In other words, the inner surface of the distal end of the balloon 30 is bonded directly to the outer surface of the inner tube 15 as shown in FIG. 2.

Figure 3:
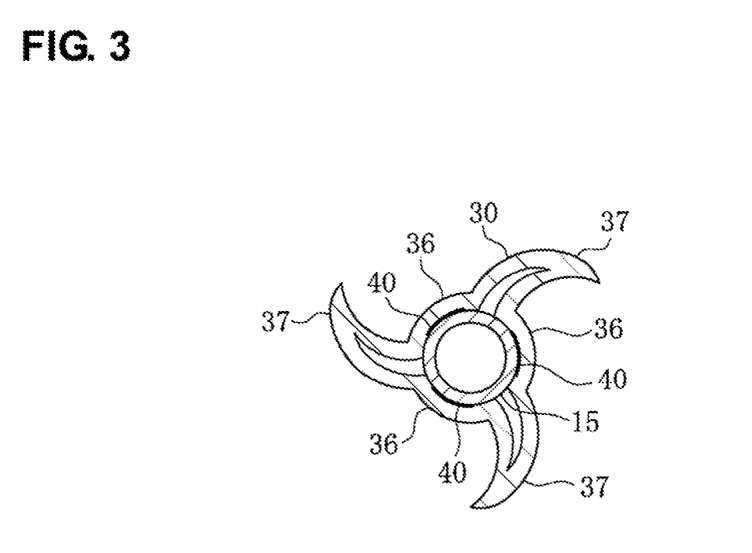
FIG. 3 is a cross-sectional view of a decreased-diameter portion of the deflated balloon.

The deflated balloon 30 has a shape as described below. The deflated balloon 30 shown in FIG. 3 is in a state of being collapsed around the inner tube 15. The collapsed balloon 30 includes contact portions 36 in contact with the inner tube 15 along a circumferential direction of the inner tube 15 and vane portions 37 protruding from the contact portions 36 in a radial direction (i.e., radially outwardly). The contact portions 36 are closely attached to the peripheral surface of the inner tube 15 (i.e., the outer surface of the inner tube 15). The vane portions 37 extend from the contact portions 36 outward in the radial direction and are bent in the circumferential direction (i.e., the vane portions 37 extend radially outwardly and possess a curve-shape in the circumferential direction). When the balloon 30 is collapsed (i.e., fully deflated), three vane portions 37 are formed in the circumferential direction and three contact portions 36 forming intermediaries between the vane portions 37 are similarly formed in the circumferential direction. Note that the three vane portions 37 are bent in the same circumferential direction (the three vane portions 37 each curve in the same circumferential direction, e.g., clockwise or counterclockwise).

The decreased-diameter portion 35 of the balloon 30 includes a connecting portion 40 connecting the balloon 30 to the peripheral (outer) surface of the inner tube 15. The connecting portion 40 is formed by connecting the three contact portions 36 spaced apart in the circumferential direction to the inner tube 15. The connecting portion 40 is denoted by a thick line in FIG. 3 for clarity. In the embodiment illustrated in FIG. 3, the connecting portion 40 is formed by fusion bonding the balloon 30 to the inner tube 15.

Figure 4:
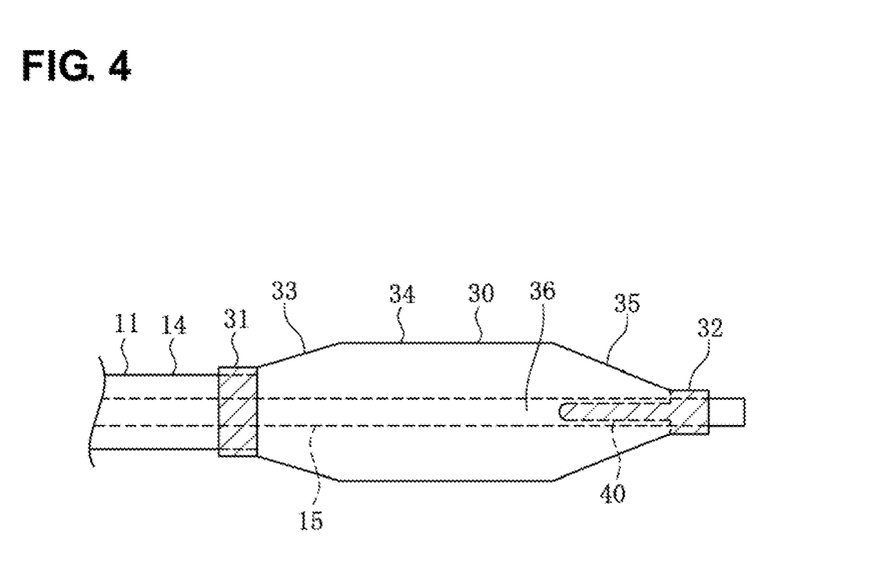
FIG. 4 is a side view of the vicinity of the deflated balloon.
Figure 5:
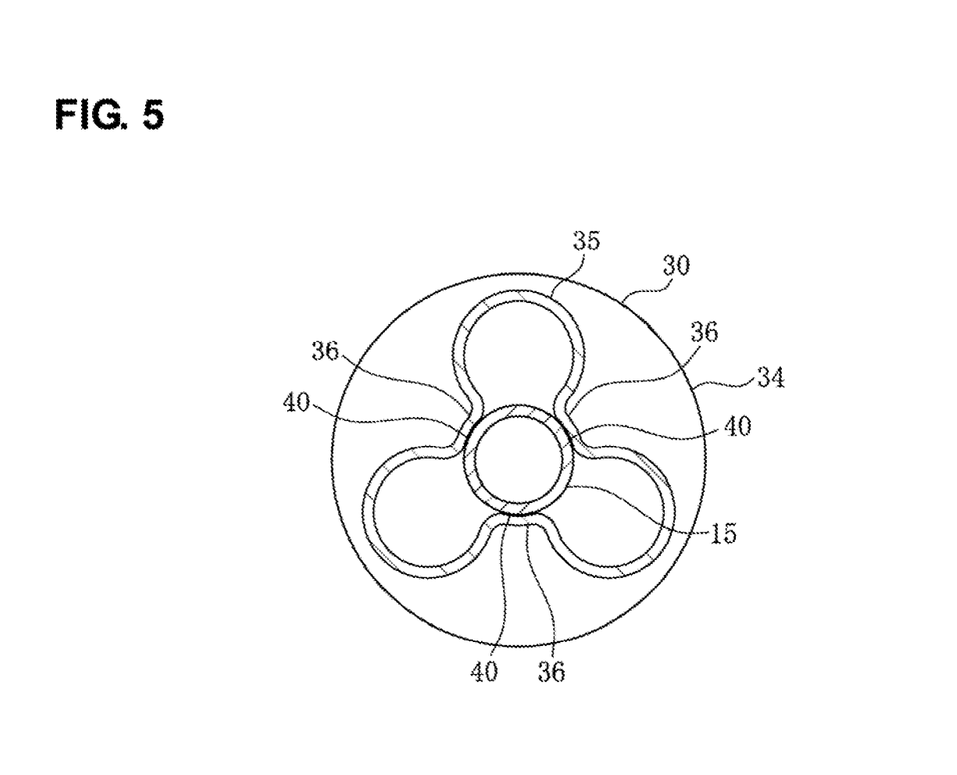
FIG. 5 is a cross-sectional view of the decreased diameter portion of the inflated balloon.

In FIG. 4, areas where the balloon 30 is fusion bonded to the catheter main body portion 11 are represented by hatching. The proximal-side fixedly bonded portion 31 of the balloon 30 is fusion bonded to the outer tube 14 along the circumferential direction and the distal-side fixedly bonded portion 32 of the balloon 30 is fusion bonded to the inner tube 15 along the circumferential direction as shown in FIG. 4. In addition, some of the areas that act as the contact portions 36 in the decreased-diameter portion 35 of the balloon 30 are fusion bonded to the inner tube 15 in the circumferential direction to form the connecting portion 40. As shown in FIGS. 4 and 5, the extent of the bond between the inner surface balloon 30 and the outer surface of the inner tube 14 at the proximal-side fixedly bonded portion 31 and at the distal-side fixedly bonded portion 32 is greater in the circumferential direction (e.g., the bond extends continuously along the circumferential direction) than the extent of the bond at the connection portion 40, which includes spaced apart portions in the circumferential direction. The axial extent of the bond at the connection portion 40, however, is greater than the axial extent of the bonds at the proximal-side fixedly bonded portion 31 or at the distal-side fixedly bonded portion 32.

The connecting portion 40 of the embodiment illustrated in FIGS. 3 and 4 is formed into a continuous linear shape from the distal-side fixedly bonded portion 32 toward the proximal side. The proximal end portion of the connecting portion 40 extends up to a proximal-side end portion of the decreased-diameter portion 35. The proximal-side end portion of the connecting portion 40 is formed into a smooth curved shape, more specifically, formed into a generally semicircular shape as shown in FIG. 4.

When the inflation fluid is delivered into the balloon 30 that is connected to the connecting portion 40 as described above to compress the balloon 30, the balloon 30 is inflated into a shape shown in FIG. 5. Portions of the contact portions 36 in the decreased-diameter portion 35 are fixedly attached to the outer surface of the inner tube 15 by the connecting portion 40. Therefore, the contact portions 36 remain closely attached to the inner tube 15. On the other hand, portions that used to be the vane portions 37 are filled with the inflation fluid to inflate. The equal-diameter portion 34 inflates to have a generally circular cross-section and deformation of the equal-diameter portion 34 caused by the connecting portion 40 is kept to a minimum.

When the balloon 30 is decompressed from the inflated state shown in FIG. 5, the balloon 30 is deflated to return back to the deflated state shown in FIG. 3. At this time, the contact portions 36 of the decreased-diameter portion 35 are closely attached to the inner tube 15 by the connecting portion 40. Owing to this, the three contact portions 36 in the circumferential direction similarly easily return to original shapes in portions of the balloon 30 proximal to the decreased-diameter portion 35. The three vane portions 37 spaced apart along the circumferential direction thus also easily return to the original shapes of the three vane portions 37. Even when the balloon 30 is repeatedly inflated and deflated a plurality of times, the contact portions 36 in the decreased-diameter portion 35 are always closely attached to the inner tube 15. Thus, it is possible to ensure that the balloon 30 returns to the original shape of the balloon 30 (i.e., the shape in the deflated position). That is, it is possible to improve re-wrappability of the balloon 30.

The proximal-side end portion of the connecting portion 40 extends in the axial direction up to the proximal-side end portion of the decreased-diameter portion 35 as illustrated in FIG. 4. This configuration helps make it possible to increase the effect of the connection portion 40 on returning the portions of the balloon 30 closer to the proximal side than the equal-diameter portion 34 to original shapes in the deflated state.

Furthermore, it is possible to prevent the connecting portion 40 from rupturing when the balloon 30 is inflated by forming the proximal-side end portion of the connecting portion 40 into the smooth curved shape. Forming the proximal-side end portion of the connecting portion into the smooth curved shape helps avoid concentration of stress on the proximal-side end portion of the connecting portion 40.

Figure 6:
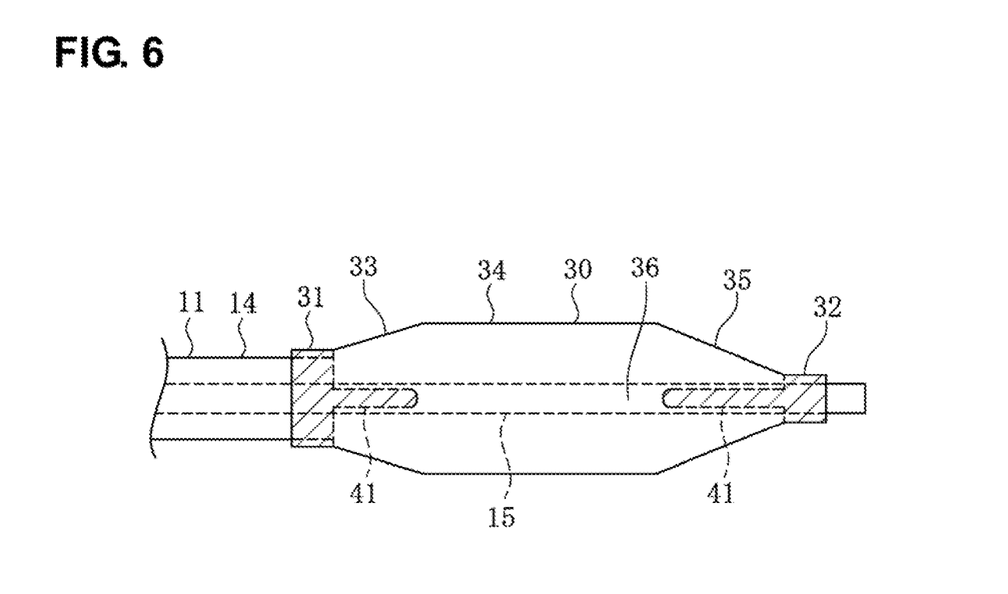
FIG. 6 is a side view of the vicinity of the balloon having connecting portions according to a first modification.

An aspect of the connecting portion 40 is not limited to the embodiment shown in FIG. 4. Connecting portions 41 according to a first modification are described next. As shown in FIG. 6, the connecting portions 41 according to the first modification are formed not only in the decreased-diameter portion 35 of the balloon 30, but also in the large-diameter portion 33. The connecting portion 41 in the decreased-diameter portion 35 has the configuration of the connecting portion 40 shown in FIG. 4. The connecting portion 41 in the large-diameter portion 33 is formed in areas of the contact portions 36 of the balloon 30 in the circumferential direction and extends linearly from the proximal-side fixedly bonded portion 31 toward the distal side in the axial direction (i.e., extends distally from the proximal-side fixedly bonded portion 31). The distal-side end portion of the connecting portion 41 extends in the axial direction up to a distal-side end portion of the large-diameter portion 33.

Providing the connecting portions 41 not only in the decreased-diameter portion 35 but also in the large-diameter portion 33 helps enable the balloon 30 to easily return to the original shape of the balloon 30 during/after deflation. The discussion below involves additional modifications of the connecting portion(s) 40 and/or 41. The discussion is based on aspects of providing a connecting portion or connecting portions only in the decreased-diameter portion 35, but the connecting portion(s) can be similarly provided not only in the decreased-diameter portion 35, but also in the large-diameter portion 33 in any of the modifications. Alternatively, the connecting portion may be provided only in the large-diameter portion 33. Furthermore, while the connecting portion 41 in the large-diameter portion 33 connects the balloon 30 to the inner tube 15, the outer tube 14 may extend into the balloon 30 and the connecting portion 41 may connect the outer tube 14 to the balloon 30.

Figure 7:
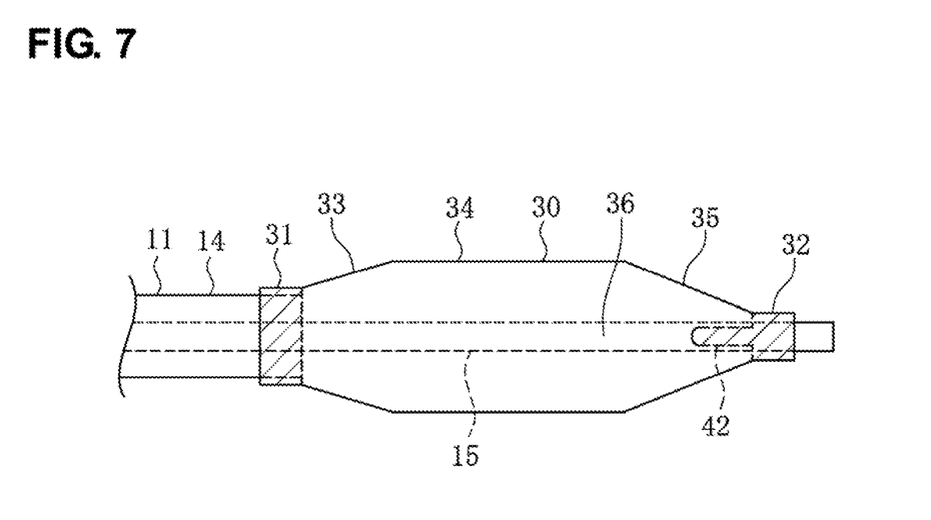
FIG. 7 is a side view of the vicinity of the balloon having a connecting portion according to a second modification.

A connecting portion 42 according to a second modification is described next. The connecting portion 42 in the modification illustrated in FIG. 7 is formed in the areas of the contact portions 36 of the balloon 30 and extends linearly from the distal-side fixedly bonded portion 32 toward the proximal side (in the axial direction). The proximal-side end portion of the connecting portion 42 extends up to an axially intermediate position of the decreased-diameter portion 35 in the axial direction (e.g., the connecting portion 42 extends to about half of the axial extent of the decreased-diameter portion 35 as shown in FIG. 7). That is, the connecting portion 42 in the present modification is shorter than the connecting portion 40 shown in FIG. 4 in the axial direction.

The axial length of the connecting portion 42 can be arbitrarily set. The force that causes the balloon 30 to return to the original shape of the balloon 30 when being deflated is weaker when the distal end of the connecting portion 42 is closer to the distal side of the decreased-diameter portion 35. In other words, the shorter that the connecting portion 42 extends in the axial direction, the weaker the force applied to restore the balloon 30 to its original shape when the balloon 30 is deflated. However, it is possible to help prevent the balloon 30 from deforming (in particular, the equal-diameter portion 34 from deforming) during inflation due to the connection of the balloon 30 to the inner tube 15 by the connecting portion 42.

Figure 8:
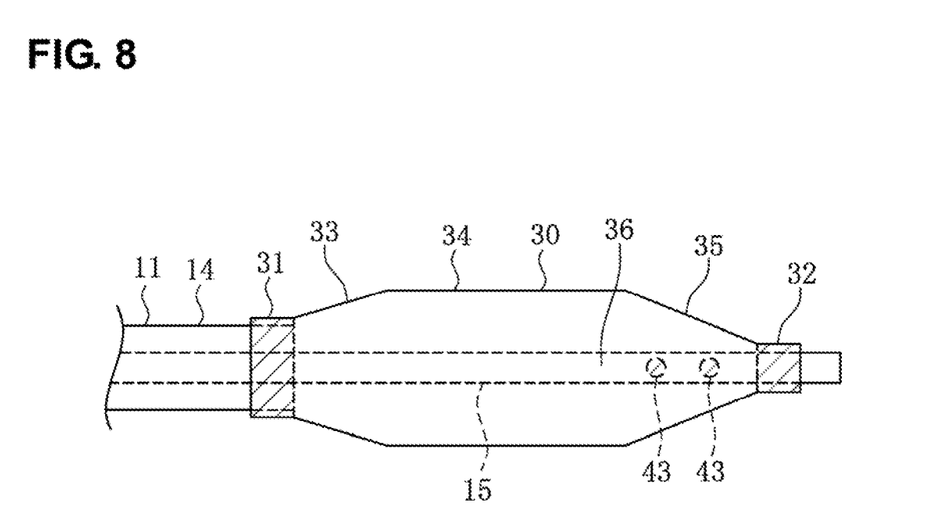
FIG. 8 is a side view of the vicinity of the balloon having connecting portions according to a third modification.
Figure 9:
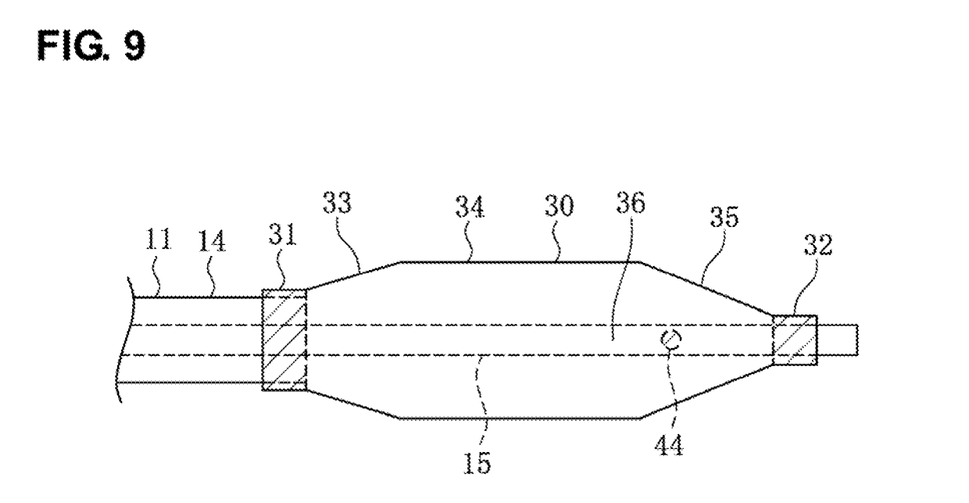
FIG. 9 is a side view of the vicinity of the balloon having a connecting portion according to a fourth modification.

Connecting portions according to third and fourth modifications are described next. The third modification illustrated in FIG. 8 includes two connecting portions 43 formed into dot shapes within a range of the decreased-diameter portion 35 of the balloon 30 in the axial direction. Positions of the connecting portions 43 in the circumferential direction are within the areas of the contact portions 36 of the balloon 30. As illustrated in FIG. 8, the connecting portions 43 are not necessarily continuously linear (i.e., the dot-shaped connecting portions 43 are spaced apart from one another in the axial direction). Furthermore, only one connecting portion 44 may be provided as shown in FIG. 9.

Figure 10:
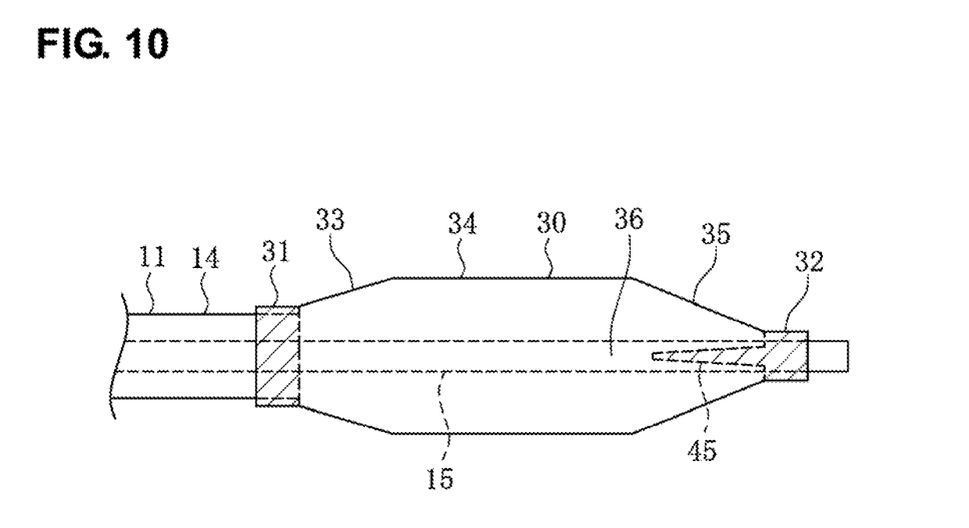
FIG. 10 is a side view of the vicinity of the balloon having a connecting portion according to a fifth modification.
Figure 11:
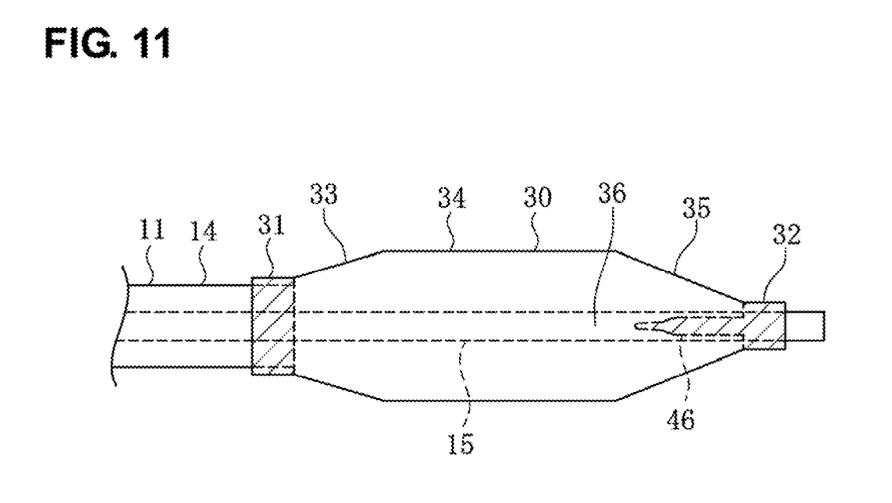
FIG. 11 is a side view of the vicinity of the balloon having a connecting portion according to a sixth modification.

Connecting portions according to fifth and sixth modifications are described next. As shown in FIG. 10, a connecting portion 45 according to the fifth modification extends from the distal-side fixedly bonded portion 32 toward the proximal side (i.e., extends from the distal-side fixedly bonded portion 32 proximally in the axial direction). The connecting portion 45 illustrated in FIG. 10 is formed such that a circumferential width (i.e., a width of the connecting portion 45 in the circumferential direction) is gradually smaller from the distal side to the proximal side. The connecting portion 45 has a generally triangular shape as a whole. The connecting portion 45 is the same as the connecting portion 40 shown in FIG. 4 in the other respects. A connecting portion 46 according to the sixth modification illustrated in FIG. 11 extends from the distal-side fixedly bonded portion 32 toward the proximal side (i.e., extends from the distal-side fixedly bonded portion 32 proximally in the axial direction). The connecting portion 46 illustrated in FIG. 10 is formed such that a circumferential width is larger on the distal side and smaller on the proximal side and that the circumferential width changes at an axially intermediate position. In other words, the connecting portion 46 possesses one portion (i.e., the distal portion) that has a constant width in the circumferential direction and possesses another portion that has a gradually decreasing (tapering) width in the circumferential direction as the connecting portion 46 extends proximally in the axial direction. In this way, the shape of the connecting portion can be set in various different ways.

Figure 12:
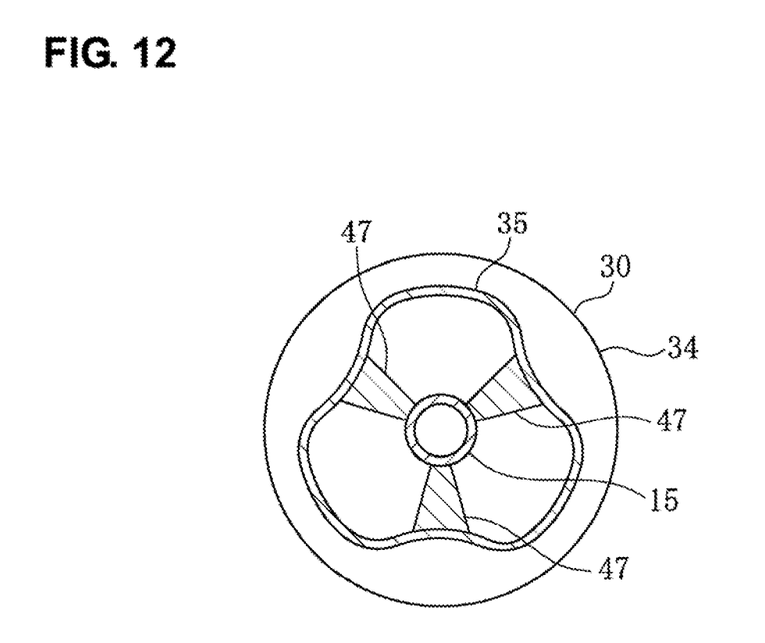
FIG. 12 is a cross-sectional view of the inflated balloon having connecting portions according to a seventh modification.

Connecting portions 47 according to a seventh modification are described next. As shown in FIG. 12, the connecting portions 47 according to the seventh modification are suspended between the inner tube 15 and the balloon 30. The connecting portions 47 are formed from an elastic material. Furthermore, the connecting portions 47 are formed within a range of the contact portions 36 of the balloon 30 in the circumferential direction and within a range of the decreased-diameter portion 35 of the balloon 30 in the axial direction.

FIG. 12 shows the balloon 30 in an inflated state. When the balloon 30 is inflated, the elastic connecting portions 47 expand together with the balloon 30. While the connecting portions 47 generate a repulsive force in a deflation direction against the expansion, it is necessary to form the connecting portions 47 to such an extent that this repulsive force does not greatly influence the shape of the equal-diameter portion 34 when the balloon 30 is inflated. An urging force of the connecting portions 47 in a deflation direction can ensure that the contact portions 36 return to the original shapes when the balloon 30 is deflated. Rubber or thermoplastic elastomer, for example, can be used as the material of the elastic connecting portions 47.

It is possible to attain the same effect as by directly fixing the balloon 30 to the catheter main body portion 11 when the connecting portions 47 are formed from the elastic material. Appropriately setting the elasticity of the connecting portion 47 also helps enable the connecting portions 47 to be provided not only in the decreased-diameter portion 35 and the large-diameter portion 33 but also in a range of the equal-diameter portion 34 in the axial direction. Moreover, shapes and the arrangement of the connection portions 47 formed from the elastic material may be those as exemplarily shown in FIG. 4 and FIGS. 6 to 11 in which the balloon 30 is directly fixed to the catheter main body portion 11.

Figure 13:
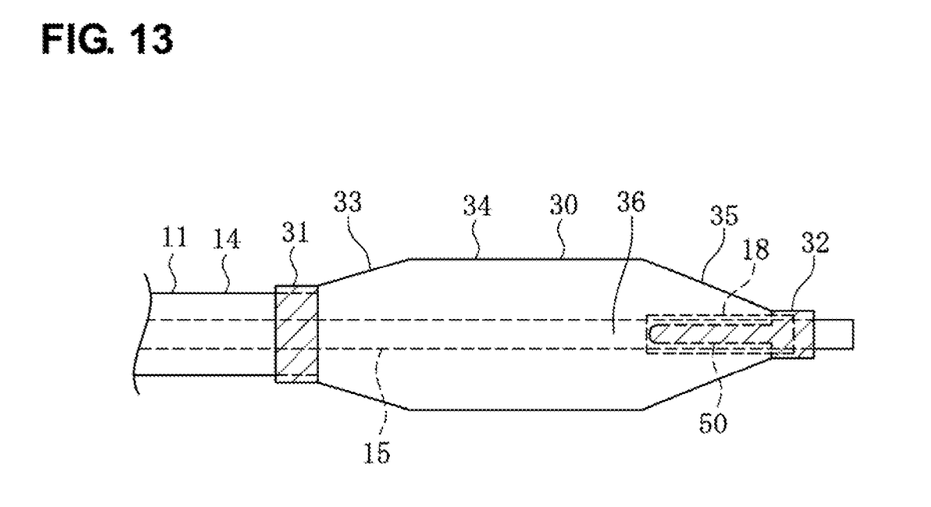
FIG. 13 is a side view of the vicinity of the balloon having a connecting portion according to an eighth modification.

Connecting portions according to eighth and ninth modifications are described next. In the eighth modification, an outer peripheral member 18 is provided on the inner tube 15 as shown in FIG. 13. The outer peripheral member 18 is formed into a tube shape (i.e., cylindrical) to have an inner diameter larger than an outer diameter of the inner tube 15. A distal-side end portion of the outer peripheral member 18 is, together with the distal-side fixedly bonded portion 32 of the balloon 30, fusion bonded to the inner tube 15. Portions other than the distal-side end portion of the outer peripheral member 18 are not constrained to a peripheral (outer) surface of the inner tube 15.

In the modification illustrated in FIG. 13, a connecting portion 50 connects the balloon 30 to the outer peripheral member 18 (i.e., the connecting portion 50 connects the inner surface of a distal portion of the balloon 30 to the outer surface of the outer peripheral member 18). The connecting portion 50 extends proximally in the axial direction (i.e., toward the proximal side) from the distal-side fixedly bonded portion 32 of the balloon 30. Thus, a portion of the outer peripheral member 18 which is connected to the connecting portion 50 is not constrained to the peripheral surface of the inner tube 15. Based on this configuration, it is possible to prevent the inner tube 15 from being pulled by the balloon 30 even though the outer peripheral member 18 is pulled radially outward (i.e., outward in the radial direction) when the balloon 30 is inflated.

When the inner tube 15 is pulled outward in the radial direction, the inner tube 15 expands. As a result, the inner tube 15 becomes thinner, which possibly causes the inner tube 15 to be more prone to being crushed and the slidability of the guide wire through the inner tube 15 to degrade (i.e., it is more difficult to slide the guide wire through the inner tube 15 if the inner tube 15 becomes thinner/the inner diameter of the inner tube 15 decreases). Providing the outer peripheral member 18 outside of the inner tube 15 and connecting the outer peripheral member 18 to the balloon 30 via the connecting portion 50 can help overcome such a problem.

Figure 14:
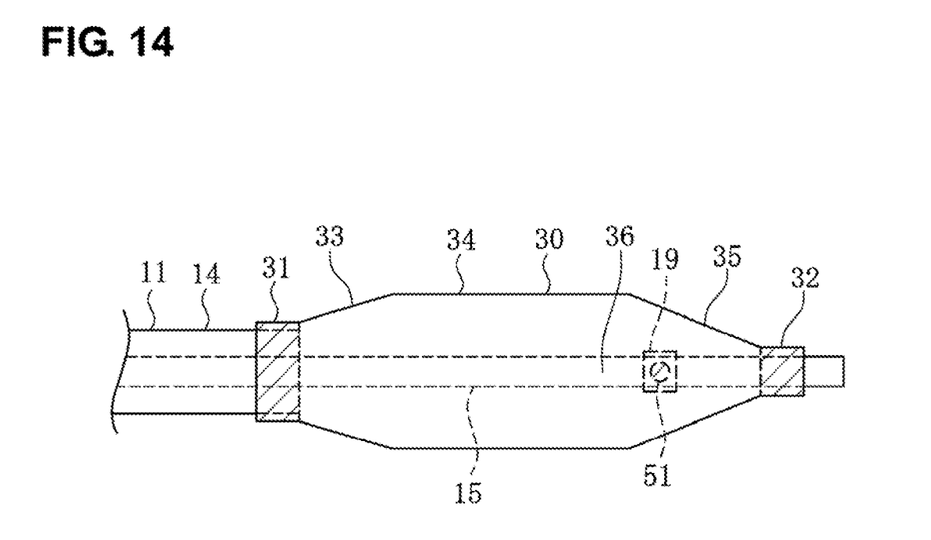
FIG. 14 is a side view of the vicinity of the balloon having a connecting portion according to a ninth modification.

In the ninth modification, a connecting portion 51 is formed into a dot shape and an outer peripheral member 19 is formed into a short tube shape to include a range in which the connecting portion 51 is formed in the axial direction as shown in FIG. 14. The outer peripheral member 19 is not fusion bonded to the inner tube 15 at all and is not constrained to the peripheral surface of the inner tube 15. When the connecting portion 51 is relatively short in the axial direction, it is thus possible to minimize expansion of the inner tube 15 in the radial direction by providing the outer peripheral member 19 only in the portion corresponding to the axially short connection portion 51. The shape of the outer peripheral member is not limited to a tube shape, but may be any shape as long as the outer peripheral member is present in at least a part of an outer periphery of the inner tube 15.

Figure 15:
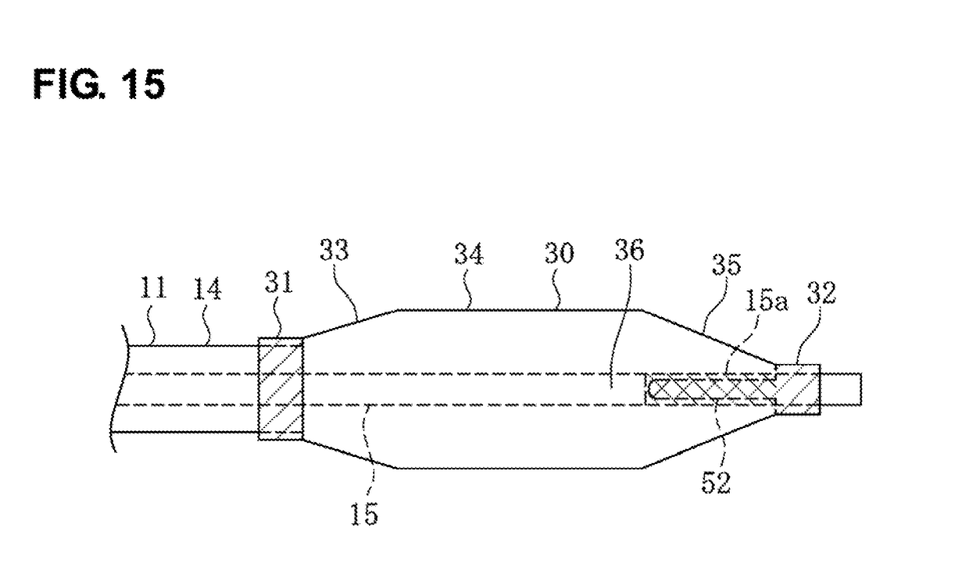
FIG. 15 is a side view of the vicinity of the balloon having a connecting portion according to a tenth modification.

Connecting portions according to tenth and eleventh modifications are described next. In the tenth modification, a part of the inner tube 15 is formed as a reinforcement portion 15*a* higher in strength than the other portions of the inner tube 15 as shown in FIG. 15. A connecting portion 52 is formed by connecting this reinforcement portion 15*a* to the balloon 30. The inner tube 15 includes the reinforcement portion 15*a* in a range in which the connecting portion 52 is formed in the axial direction.

The reinforcement portion 15*a* can be formed by making a corresponding portion of the inner tube 15 thicker (i.e., more thick relative to the remainder of the inner tube 15) when the inner tube 15 is manufactured. Alternatively, the reinforcement portion 15*a* may be formed by manufacturing the inner tube 15 having a uniform thickness, covering a part of the inner tube 15 with another tube-shaped member, and integrating the part of the inner tube 15 with the covering tube-shaped member by fusion bonding, adhesive bonding or the like.

Figure 16:
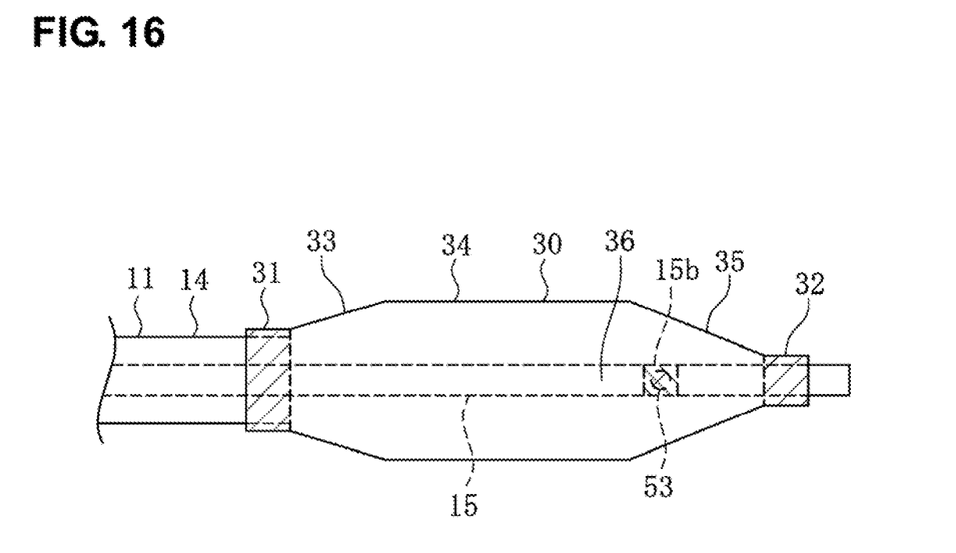
FIG. 16 is a side view of the vicinity of the balloon having a connecting portion according to an eleventh modification.

A connecting portion 53 is formed into a dot shape and a reinforcement portion 15*b* is formed only in a portion corresponding to this connecting portion 53 in the eleventh modification as shown in FIG. 16.

Providing the reinforcement portion on the inner tube 15 can suppress the expansion of the inner tube 15 when the balloon 30 is inflated (i.e., a force to pull the inner tube 15 outward in the radial direction can be suppressed) by the connecting portion.

As described above, the balloon catheter 10 according to the present embodiment includes the elongated catheter main body portion 11 and a balloon 30 provided on the distal side of the catheter main body portion 11. The balloon 30 is inflatable (i.e., the balloon is able to be inflated and deflated). The catheter main body portion 11 includes the hollow outer tube 14 and the hollow inner tube 15 disposed within the outer tube 14. The balloon 30 is collapsed to include the contact portion 36 in contact with the inner tube 15 and the vane portion 37 protruding from the contact portion 36 in the radial direction when the balloon 30 is in a deflated state. The balloon 30 includes the connecting portion 40 in the contact portion 36 to connect the balloon 30 to the catheter main body portion 11. Even when the balloon 30 is repeatedly inflated and deflated a plurality of times, the contact portion 36 is always connected to the inner tube 15 by the connecting portion 40. This configuration thus helps ensure that the balloon 30 returns to the original shape when the balloon 30 is deflated. That is, it is possible to improve the re-wrappability of the balloon 30 without the need to attach the external member to the balloon 30 from outside.

By configuring the balloon catheter 10 such that the catheter main body portion 11 includes the hollow outer tube 14 and the hollow inner tube 15 disposed within the outer tube 14, the proximal side of the balloon 30 is fixed to the outer tube 14, the distal side of the balloon 30 is fixed to the inner tube 15, and the connecting portion 40 is formed by being fixedly bonded to the peripheral surface of either the outer tube 14 or the inner tube 15, then the connecting portion 40 can be formed only by fixedly bonding the balloon 30 to the peripheral surface of either the outer tube 14 or the inner tube 15, and it is possible to facilitate manufacturing.

By configuring the balloon catheter 10 such that the balloon 30 includes the large-diameter portion 33 having the diameter larger from the proximal side toward the distal side, the equal-diameter portion 34 continuous with the large-diameter portion 33 and having the generally equal diameter along the axial direction, and the decreased-diameter portion 35 continuous with the equal-diameter portion 34 and having the diameter smaller from the proximal side to the distal side, and the connecting portion 40 is not present in the equal-diameter portion 34, it is possible to help avoid the influence of the connecting portion 40 on the shape of the equal-diameter portion 34 that is an effective portion during treatment.

By configuring the balloon catheter 10 such that the connecting portion 40 is formed by linearly and fixedly bonding the balloon 30 to the inner tube 15 from the fixedly bonded portion 31 or 32 where the balloon 30 is fixed to either the outer tube 14 or the inner tube 15 to a central side of the balloon 30, it is possible to increase a connection strength for connecting the balloon 30 to the inner tube 15 by the connecting portion 40 and to prevent the separation (rupture) of the connecting portion 40 when the balloon 30 is inflated.

By configuring the balloon catheter 10 such that the connecting portion 42 is formed by fixedly bonding the balloon 30 to the inner tube 15 in a dot manner from the fixedly bonded portion 31 or 32 where the balloon 30 is fixed to either the outer tube 14 or the inner tube 15 to a central side of the balloon 30, then a fixedly bonded area can be made small, and it is, therefore, possible to facilitate manufacturing.

By configuring the balloon catheter 10 such that the end portion, which is closer to the central side of the balloon 30, of the connecting portion 40 is formed into the smooth curved shape, then it is possible to avoid the concentration of a stress on the central-side end portion of the connecting portion 40, and it is possible to prevent the separation (rupture) of the connecting portion 40 when the balloon 30 is inflated.

By configuring the balloon catheter 10 such that the catheter main body portion 11 includes the hollow outer tube 14 and the hollow inner tube 15 disposed within the outer tube 14, the proximal side of the balloon 30 is fixed to the outer tube 14, the distal side of the balloon 30 is fixed to the inner tube 15, and the connecting portion 47 is formed from the elastic material suspended between the balloon 30 and either the outer tube 14 or the inner tube 15, it is possible to provide the connecting portion 47 in a broad range of the balloon 30 including the equal-diameter portion 34 by appropriately setting elasticity of the connecting portion 47.

By configuring the balloon catheter 10 such that the inner tube 15 includes the outer peripheral member 18 in at least a part of the outer periphery within the balloon 30, the connecting portion 50 connects the balloon 30 to the outer peripheral member 18, and the outer peripheral member 18 is not constrained to the peripheral surface of the inner tube 15 in a range in which at least the connecting portion 50 is connected to the outer peripheral member 18 in the axial direction, then it is possible to prevent the inner tube 15 from being pulled outward by the connecting portion 50 when the balloon 30 is inflated, and it is possible to prevent degradation of the slidability of the guide wire due to the expansion of the inner tube 15.

By configuring the balloon catheter 10 such that the inner tube 15 includes the reinforcement portion 15a having the increased strength in a range connected by at least the connecting portion 52 in the axial direction, it is possible to prevent degradation of the slidability of the guide wire due to the reduction of the strength of the pulled portion of the inner tube 15 even if the inner tube 15 is pulled outward by the connecting portion 52 when the balloon 30 is inflated.

While the balloon catheter described above is an over-the-wire type, the balloon catheter may be a rapid-exchange type.

The configurations of the above described embodiments are given as preferred embodiments. The configuration of the balloon catheter disclosed in this application is not limited to any of these specific configurations. That is, various modifications can be made within a scope within which the same advantages and effects can be exhibited. For example, while the proximal-side end portion of the connecting portion is formed into the smooth curved shape by way of example, the shape of the proximal-side end portion may be a triangular or a quadrangular shape.

The detailed description above describes a balloon catheter. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon catheter comprising:
an elongated catheter main body portion extending in an axial direction, the catheter main body portion possessing a distal portion and a proximal portion proximal to the distal portion in the axial direction;
a balloon provided on the distal portion of the catheter main body portion, the balloon being inflatable to expand radially outward into an inflated state and deflatable to contract radially inward into a deflated state;
the catheter main body portion comprising a hollow outer tube and a hollow inner tube disposed within the outer tube, the outer and inner tubes extending in the axial direction, the outer and inner tubes each possessing an inner surface and an outer surface;
the balloon comprising a contact portion that contacts the outer surface of the inner tube and a vane portion protruding from the contact portion radially outward when the balloon is in the deflated state;
the contact portion of the balloon comprising a connecting portion that connects the balloon to the catheter main body portion;
the balloon possessing an inner surface, a proximal end and a distal end;
the proximal end of the balloon being fixed to the outer surface of the outer tube;
the distal end of the balloon being fixed to the outer surface of the inner tube; and
the connecting portion being an elastic material suspended between the inner surface of the balloon and the outer surface of at least one of the outer tube and the inner tube.

2. The balloon catheter according to claim 1, wherein the connecting portion fixedly bonds the outer surface of at least one of the outer tube or the inner tube to the inner surface of the balloon.

3. The balloon catheter according to claim 2, wherein the balloon possesses an outer diameter in the inflated state,
the balloon comprises a large-diameter portion, the outer diameter of the balloon increasing from a proximal end of the large-diameter portion to a distal end of the large-diameter portion,
the balloon comprises an equal-diameter portion, the outer diameter of the balloon being generally equal from a proximal end of the equal-diameter portion to a distal end of the equal-diameter portion in the axial direction, the proximal end of the equal-diameter portion being continuous with the distal end of the large-diameter portion,
the balloon comprises a decreased-diameter portion, the outer diameter of the balloon decreasing from a proximal end of the decreased-diameter portion to a distal end of the decreased-diameter portion, the proximal end of the decreased-diameter portion being continuous with the distal end of the equal-diameter portion, and
the equal-diameter portion is devoid of the connecting portion.

4. The balloon catheter according to claim 3, wherein the connecting portion extends continuously and linearly in the axial direction to fixedly bond the inner surface of the balloon to the outer surface of the inner tube.

5. The balloon catheter according to claim 3, wherein at least a portion of the connecting portion is dot shaped and spaced apart from the distal and proximal ends of the balloon in the axial direction.

6. The balloon catheter according to claim 3, wherein the connecting portion comprises a first end and a second end, the first end being at one of the distal end or the proximal end of the balloon, the second end being a smooth curved shape.

7. The balloon catheter according to claim 1, further comprising
an outer peripheral member extending in the axial direction and positioned around the inner tube within the balloon, the connecting portion connecting the balloon to the outer peripheral member, and the outer peripheral member not being constrained to the outer surface of the inner tube along a range in which the connecting portion is connected to the outer peripheral member in the axial direction.

8. The balloon catheter according to claim 1, wherein the inner tube includes a reinforcement portion having an increased strength along a range of the connecting portion in the axial direction.

9. A balloon catheter comprising:
an elongated catheter main body portion extending in an axial direction from a proximal end to a distal end, the catheter main body portion possessing a radial direction;
the catheter main body portion comprising a cylindrical outer tube and a cylindrical inner tube within the outer tube, the outer tube possessing a distal end and the inner tube extending in the axial direction distally beyond the distal end of the outer tube, the inner and outer tubes each possessing an inner surface and an outer surface;
a balloon connected to the inner tube and to the outer tube of the catheter main body portion, the balloon being inflatable to expand radially outward into an inflated state and deflatable to contract radially inward into a deflated state, the balloon possessing an inner surface;
a plurality of connecting portions fixedly bonding the inner surface of the balloon to the outer surface of at least one of the inner tube and the outer tube, the connecting portions being spaced apart from one another in a circumferential direction of the balloon catheter;
the balloon comprising a plurality of vane portions, each of the vane portions being adjacent to the connecting portions so that the vane portions and the connecting portions alternate in the circumferential direction, the vane portions protruding radially outward beyond the balloon at the connecting portions when the balloon is in the deflated state; and
the vane portions of the balloon inflating and extending radially outwardly when the balloon is in the inflated state, the connecting portions preventing the balloon from expanding radially outward at the connecting portions during inflation.

10. The balloon catheter according to claim 9, wherein a number of the connecting portions and the vane portions is three, the connecting portions being evenly spaced apart from one another in the circumferential direction.

11. The balloon catheter according to claim 10, wherein each of the connecting portions extend from the distal end of the balloon proximally in the axial direction.

12. The balloon catheter according to claim 10, wherein at least a portion of each of the connecting portions is dot-shaped and is spaced apart from the distal end and the proximal end of the balloon in the axial direction.

13. The balloon catheter according to claim 10, wherein the balloon possesses an outer diameter in the inflated state, the balloon comprises a large-diameter portion, the outer diameter of the balloon increasing from a proximal end of the large-diameter portion to a distal end of the large-diameter portion, the balloon comprises an equal-diameter portion, the outer diameter of the balloon being generally equal from a proximal end of the equal-diameter portion to a distal end of the equal-diameter portion in the axial direction, the proximal end of the equal-diameter portion being continuous with the distal end of the large-diameter portion, the balloon comprises a decreased-diameter portion, the outer diameter of the balloon decreasing from a proximal end of the decreased-diameter portion to a distal end of the decreased-diameter portion, the proximal end of the decreased-diameter portion being continuous with the distal end of the equal-diameter portion, and the equal-diameter portion is devoid of the connecting portions.

14. The balloon catheter according to claim 13, wherein each of the connecting portions extend from the distal end of the decreased-diameter portion to the proximal end of the decreased-diameter portion in the axial direction.

15. A balloon catheter comprising:
an elongated catheter main body portion extending in an axial direction, the catheter main body portion possessing a distal portion and a proximal portion proximal to the distal portion in the axial direction;
a balloon provided on the distal portion of the catheter main body portion, the balloon being inflatable to expand radially outward into an inflated state and deflatable to contract radially inward into a deflated state;
the catheter main body portion comprising a hollow outer tube and a hollow inner tube disposed within the outer tube, the outer and inner tubes extending in the axial direction, the outer and inner tubes each possessing an inner surface and an outer surface;
the balloon comprising a contact portion that contacts the outer surface of the inner tube and a vane portion protruding from the contact portion radially outward when the balloon is in the deflated state;
the contact portion of the balloon comprising a connecting portion that connects the balloon to the catheter main body portion;
the balloon comprising a large-diameter portion, the outer diameter of the balloon increasing from a proximal end of the large-diameter portion to a distal end of the large-diameter portion;
the balloon comprising a decreased-diameter portion, the outer diameter of the balloon decreasing from a proximal end of the decreased-diameter portion to a distal end of the decreased-diameter portion; and
the connecting portion being fixed between an inner surface of the large-diameter portion of the balloon or an inner surface of the decreased-diameter portion of the balloon and the outer surface of at least one of the outer tube and the inner tube.

16. The balloon catheter according to claim 15, wherein the inner tube includes a reinforcement portion having an increased strength along a range of the connecting portion in the axial direction.

17. The balloon catheter according to claim 15, wherein the connecting portion is an elastic material suspended between the inner surface of the balloon and the outer surface of the outer tube or the inner tube.

* * * * *